United States Patent [19]
Hamilton

[11] Patent Number: 4,774,092
[45] Date of Patent: Sep. 27, 1988

[54] INGESTIBLE CAPSULES

[75] Inventor: Robert J. Hamilton, New South Wales, Australia

[73] Assignee: ICI Australia Limited, Melbourne, Australia

[21] Appl. No.: 26,445

[22] PCT Filed: Jun. 23, 1986

[86] PCT No.: PCT/AU86/00180
§ 371 Date: Feb. 18, 1987
§ 102(e) Date: Feb. 18, 1987

[87] PCT Pub. No.: WO87/00045
PCT Pub. Date: Jan. 15, 1987

[30] Foreign Application Priority Data

Jun. 24, 1985 [AU] Australia ............................. PH1174

[51] Int. Cl.⁴ ................................................ A61K 9/48
[52] U.S. Cl. ..................................... 424/453; 424/451;
424/454; 424/462; 206/528; 206/524.6;
206/524.7
[58] Field of Search ............... 424/451, 454, 456, 453,
424/455, 900, 419; 425/804; 428/321.5; 53/266
R; 206/528, 524.6, 524.7

[56] References Cited

U.S. PATENT DOCUMENTS

| | | | |
|---|---|---|---|
| 3,149,038 | 9/1964 | Jeffries | 424/482 |
| 3,379,554 | 4/1968 | Brindamour | 427/3 |
| 4,428,926 | 1/1984 | Keith | 424/482 |
| 4,431,965 | 2/1984 | Keith et al. | 424/449 |

Primary Examiner—Thurman K. Page
Assistant Examiner—L. R. Horne
Attorney, Agent, or Firm—Cushman, Darby & Cushman

[57] ABSTRACT

A capsule for use in administering therapeutic agents to animals is made from a blend of
(i) from 10–75% by weight of a material chosen from polyalkylene glycols of average molecular weight of from 2,000–20,000; and
(ii) from 20–80% by weight of poly(ethylene oxide) of average molecular weight of from 80,000–1×10⁷.

The preferred materials are polyethylene glycol of average molecular weight 3,000–5,000 and poly (ethylene oxide) of average molecular weight 300,000–800,000. It is possible to include therapeutic agents in the composition of the capsule as well as in its cavity. The capsules of this invention find particular application in the administering of trace elements, especially copper oxide needles, to animals.

25 Claims, 5 Drawing Sheets

INGESTIBLE CAPSULES

This invention relates to devices and methods for the therapeutic treatment of animals and in particular to the oral administration of therapeutic agents to animals.

The therapeutic treatment of non-human animals, such as for example, cattle, sheep, horses, goats, pigs, cats and dogs, parallels that of humans in many respects both in types of conditions and diseases. However, the methods of administering therapeutic agents to such animals are frequently different from those used with humans. Thus, for example, cattle and sheep which graze on particular pastures and acquire trace element deficiencies are of necessity given a supplemental diet comprising trace element material since removal to better pastures is frequently impossible or too costly. Similarly, such animals cannot be removed from exposure to environments which lead to infections with varied endoparasites and must therefore be treated while under continuing exposure to infection. In such cases, new methods of administration of therapeutic agents have been developed to overcome difficulties of administration. Typically whole herds of animals must be treated in a short space of time to keep labour costs low, and slow release compositions may need to be employed to avoid the repetitive doses commonly used with humans. Again, the animals referred to above have particular physical charateristics and behaviour which make them less amenable to handling and dosing than humans. In some cases physiological differences may affect the type and method of treatment and this is particularly so in the case of ruminants as will be explained hereinafter.

Thus the oral methods of administration of liquid and solid therapeutic agents to humans, namely, liquids or syrups, tablets and capsules have had to be substantially modified for use with animals. Liquids, for example, are commonly administered to animals by a drench gun comprising a long tube so that the liquid enters at a point beyond the oral cavity and is thus not readily expectorated.

Gelatin capsules are at present widely used in the administration of therapeutic agents to both human and non-human animals.

While gelatin capsules are economic to produce on a commercial scale their use in administration to non-human animals has given rise to problems. The gelatin capsules are difficult to administer to animals, particularly ruminant animals.

The properties of the gelatin renders this procedure difficult since the capsules readily become limp on exposure to moisture (rain, saliva etc). Consequently it is difficult to administer such capsules by means of dosing guns commonly used in the art. Gelatin capsules rapidly become limp when exposed to animal saliva which tends to accumulate in such guns. Furthermore, softening of the capsules often results in premature bursting and release of the therapeutic agent so that the agent is not properly delivered. This problem is further exacerbated if the capsule filling is heavy.

In general, animals to be treated with the capsules have to be securely held by the doser who must place the gelatin capsule behind the tongue of the animal to prevent regurgitation and expectoration. Even with small animals such as cats and dogs the administration of gelatin capsules is difficult.

Heavy boluses or bullets have been used as alternatives to such capsules, and these are usually designed for a particular therapeutic agent, often with controlled release as a critical factor.

We have found that capsules of high molecular weight poly (ethylene oxide), for example poly (ethylene oxide) of molecular weight in the range 500,000 to 4,000,000, are more rigid than gelatin capsules and overcome some of the problems associated with the moisture sensitivity of gelatin capsules.

However although high molecular weight poly (ethylene oxide) capsules have some advantages over conventional capsules, poly (ethylene oxide) is difficult to form into capsules and is a comparatively expensive material.

It is an object of our invention to provide an inexpensive capsule which may be economically produced on a commercial scale.

It is also an object of our invention to provide a capsule which facilitates oral administration of therapeutic agents to animals, and which is adaptable to a wide range of animals and to a wide range of therapeutic agents.

It is a further object of our invention to provide a capsule for the purpose defined hereinbefore, which can be readily filled with a therapeutic agent by the end-user on a one-off basis without special filling apparatus being required.

We have now found that a rigid capsule of good strength may be produced using a composition comprising up to 75% polyalkylene glycols of average molecular weight in the range 2,000 to 20,000.

Accordingly we provide a capsule for the administration of one or more therapeutic agents to animals wherein said capsule comprises:

(i) 10 to 75% by weight material chosen from polyalkylene glycols of average molecular weight in the range 2,000 to 20,000; and (ii) 20 to 80% by weight poly (ethylene oxide) of average molecular weight in the range 80,000 to $1 \times 10^7$.

Typical polyalkylene glycols may include:

polymers prepared from condensation of one or more monomers selected from the group ethylene oxide, propylene oxide and butylene oxide;

block copolymers comprising blocks of condensed ethylene oxide, propylene oxide and/or butylene oxide;

esters of the aforementioned polyalkylene glycols such as, for example, the condensation products of fatty acids with ethylene oxide, propylene oxide, butylene oxide or mixtures thereof;

ethers of the abovementioned polyalkylene glycols such as, for example the condensation products of alcohols or phenols with ethylene oxide, propylene oxide butylene oxide or mixtures thereof;

amine alkoxylates such as, for example, the condensation products of ammonia, alkylamines or dialkylamines with ethylene oxide, propylene oxide, butylene oxide or mixtures thereof.

Preferred said alkylene glycols may be chosen from the group of polyethylene glycol, polypropylene glycol, "Teric" N100 which is the product of condensation of nonyl phenol with 100 ethylene oxide units, "Teric" X100 (octylphenyl condensed with 100 ethylene oxide units) and "Teric" 16A50 ($C_{16}$ fatty acid alcohol condensed with 50 ethylene oxide units) ("Teric" is a trade mark.) Most preferred alkylene glycol is polyethylene glycol.

The size and shape of the capsule is not narrowly critical and capsules can assume a wide variety of sizes and shapes subject to the particular application for which the capsule will be used. Thus, for example, the capsules may be cylindrical, spherical, spheroidal, elliptical or any other form that is generally free of sharp edges and protuberances that would hinder the administration and ingestion of the capsules. In general the capsule must not be so large that it is likely to block the throat or oesophageal passage, nor so small that it is difficult to hold.

We have found that the composition comprising the capsules of the present invention is thermoplastic and capsules of the present invention may be made by the conventional processes used for the moulding of thermoplastics, such as, for example, by injection molding, and extrusion processes. It is a particular feature of our invention that the capsules may be conveniently manufactured by injection moulding techniques.

We have found that compositions comprising a substantial proportion of polyethylene glycol may be injection moulded on a commercial scale. For example, compositions comprising 65% polyethylene glycol 4,000 (which has an average molecular weight of approximately 4,000) and 35% polyethylene oxide of molecular weight of about 600,000 have proved to be particularly successful.

Moreover we have found that compositions containing a significant proportion of polyethylene glycol provide particular advantages in the moulding process. Compositions comprising larger proportions of polyethylene glycol may be injection moulded under milder conditions providing a significant economic advantage.

For example, mixtures of 60 parts polyethylene glycol 4,0000 and 35 parts polyethylene oxide (average molecular weight approximately 600,000) may be moulded using injection pressures of about 570 kg/cm$^2$ at a temperature of about 140°. In contrast, compositions comprised essentially of poly(ethylene oxide) require much higher temperature and pressure conditions; for example it may be necessary to use pressures of 1300 kg/cm$^2$ or higher at temperatures of 200° C. or more in order to achieve successful injection moulding.

It is surprising that polyethylene glycol of such a low molecular weight can be incorporated into poly(ethylene oxide) in such high proportions and still provide an injection mouldable thermoplastic composition.

Consequently in a preferred embodiment of the present invention there is provided a capsule as hereinbefore described wherein said capsule comprises:
(i) 35 to 75% by weight polyethylene glycol of average molecular weight in the range 2,000 to 12,000; and
(ii) 25 to 65% by weight poly (ethylene oxide) of average molecular weight in the range $1 \times 10^5$ to $1 \times 10^7$.

Most preferably said capsule comprises:
(i) 50 to 70% by weight polyethylene glycol of average molecular weight in the range 2,000 to 12,000; and
(ii) 35 to 50% by weight poly (ethylene oxide) of average molecular weight in the range $1 \times 10^5$ to $1 \times 10^7$.

Typically the ratio of polyethylene glycol to polyethylene oxide is in the range 0.15 to 2.5 weight/weight.

It is preferred that the ratio of polyethylene glycol to poly(ethylene oxide) in said composition be in the range of 0.5 to 2.5. More preferably the ratio of polyethylene glycol to poly(ethylene oxide) is in the range of 1 to 2.5.

Preferably the average molecular weight of said polyethylene glycol will be in the range 2,500 to 6,000.

Most preferably the average molecular weight of said polyethylene glycol is in the range 3,000 to 5,000.

Preferably the average molecular weight of said poly (ethylene oxide) will be in the range $1 \times 10^5$ to $1 \times 10^6$. Most preferably poly(ethylene oxide) has an average molecular weight in the range 300,000 to 800,000.

Unlike gelatin capsules heretofore commonly used in administration of therapeutic agents, the polyethylene glycol capsules of the present invention are suitable for administration using balling guns or pellet dispensing guns known to those skilled in the art. Multiple dosing of animals, example ruminant animals, using such guns, provides a significant time saving advantage for farmers.

The heretofore used capsules generally comprise a body part and a head part of U-shaped cross section wherein the diameter of the head part is slightly larger enabling the head part to slide over the body part. However, capsules of this shape are generally difficult to administer by means of a dispensing gun.

We have found that capsules comprising a head part and body part which when engaged provide a uniform diameter of said head part and said body part at the point of their exterior junction are particularly useful. The smooth surface thereby provided allows the capsule to more easily pass through the sleeve of the dosing gun.

Preferably such capsules have an approximately cylindrical shape.

It may be particularly advantageous to have a capsule of a size that fits commercially available dispensing guns of the type commonly used for dispensing pellets.

The commercial guns usually have a resilient sleeve with an inside diameter of 12-14 mm. The length of the capsule is not narrowly critical but is conveniently not greater that the maximul length that can be ejected by the pellet dispensing gun. For readily available dispensing guns the maximum length is typically 40-50 mm. The length of the capsule may be chosen so that the internal cavity is just sufficient to contain the dosage unit of the therapeutic agent.

A particular embodiment of the capsules of the present invention will now be illustrated with reference to the appended drawings.

In the appended drawings:
FIG. 1 shows the shape of head and body parts of a capsule of one embodiment of the present invention.
FIG. 2 shows a longitudinal cross section of an assembled capsule
FIG. 3 shows the head and body parts of a first specific example of a capsule
FIG. 4 shows the head and body parts of a second specific example of a capsule.
FIG. 5 shows the design of a moulding plate of a die to be used in the production of capsules according to FIG. 3.

Referring to the drawings, in FIG. 1 is shown a capsule consisting of a head part (1) and a body part (2). The body part has a recessed edge (3) to engage the head part, and both head and body parts have internal cavities to contain one or more therapeutic agents.

FIG. 2 shows a longitudinal cross section of an assembled capsule of the type shown in FIG. 1. The recessed edge (3) of the body part (2) is engaged with the head part (1) to provide an enclosed space or cavity (4) which may contain one or more therapeutic agents. The head and body parts have an approximately equal external diameter at the point of junction (5) of the head and body parts.

Figure 1:
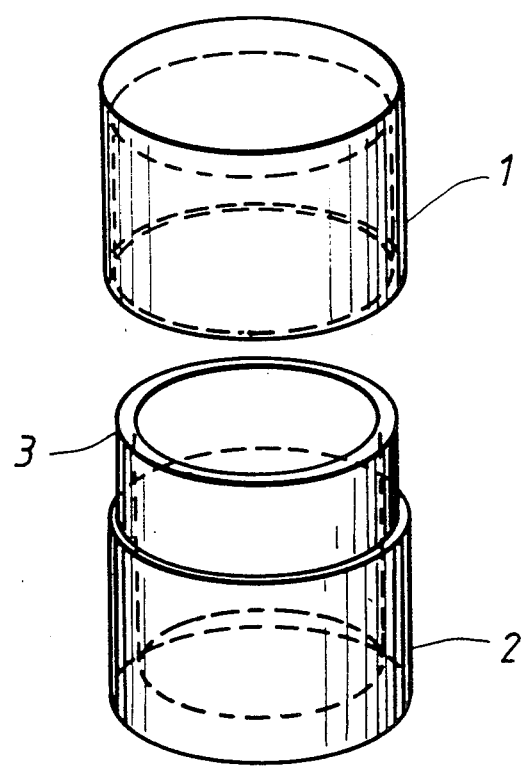
Figure 2:
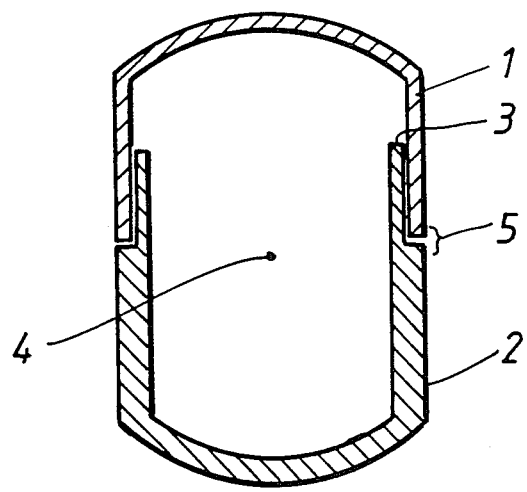
Figure 3:
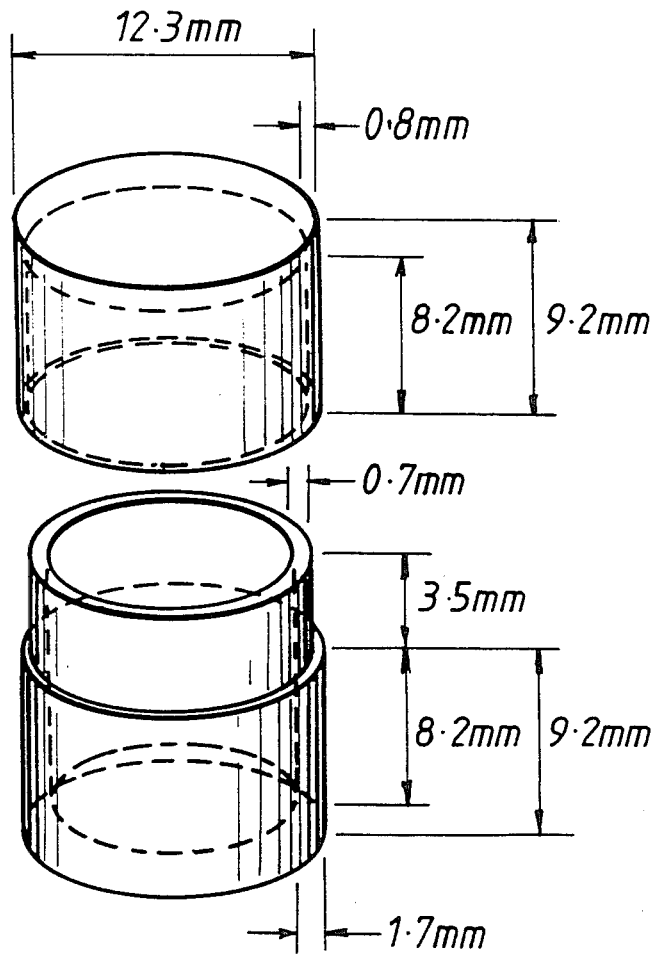
FIG. 3 shows head and body parts of a capsule which may be of convenient size particularly for administration to sheep. The capsule may be administrated for example by means of a conventional dispensing gun suitable for the purpose.

The capsules shown in FIG. 1 to FIG. 3 may be particularly useful for administration to animals by means of dosing guns known to those in the art for use in the administration of pellets. In general such guns have a long sleeve which is placed down the gullet of the animal to allow delivery of a dose to a point behind the tongue thereby reducing the likelihood of expectoration. Delivery using this method may be particularly preferred in dosing ruminant animals.

Capsules dispensed by hand might conveniently be of polygonal, for example, hexagonal, cross-section so that they do not roll when placed on a slightly inclined surface such as a table. The process used to make the capsule or the equipment used on a commercial scale to fill the capsule may be a significant factor in choosing an appropriate shape.

Capsules of our invention made by an injection moulding technique are highly uniform in size and can readily be filled and sealed by conventional capsule-filling equipment and, more importantly, by high-speed microprocessor-controlled equipment.

The capsules of our invention are readily sealed by heat-sealing techniques, by the application of a film of water on the joining surfaces before the cap and body sections are brought into contact, or by having in the design of the capsule inter-locking engaging portions on the cap and body section. Edge-sealing adhesives may also be used. Such adhesives may be water-soluble or water-dispersible but this is not essential since the capsules of our invention are readily dissolved in aqueous body fluids, thus releasing the contents without the need for the cap and body sections to specifically separate.

The capsules of our invention are essentially self-lubricating because of the properties of the polyethylene glycol but additional lubricants may be added to the composition if desired. Typical lubricants which are suitable for inclusion in the composition used to prepare the capsules may be chosen from silicones and the stearates of the elements aluminium, calcium, magnesium and tin and may constitute from 0.1 to 10% w/w of the total material used to prepare the capsule.

Plasticizers may also be included in the capsule compositions and may be used to aid the forming or molding process. Typical plasticizers such as for example glycerol; sorbitol; dioctyl sodium sulpho-succinate; triethyl citrate; tributyl citrate; 1,2-propylene glycol; the mono-, di-, triactelates of glycerol may be used, in a range of 0.5–10% w/w of the compositions.

The compositions may also optionally contain other additives known to those skilled in the art such as for example colourants, including dyes and pigments, and extenders or fillers.

In some cases, for example in capsules for human use, it may be advantageous to include in the composition extenders in a range of for example up to 40% w/w or more of the composition. Because of the high acidity of the human stomach basic extenders such as for example talc and calcium carbonate may aid dissolution of the capsule. In general capsules for use in ruminant animals may optionally comprise up to 10% w/w such extenders although more maybe used if desired.

Typical pigments may include titanium oxide, red ochre, yellow ochre, and ultramarine blue. Where present in the capsule composition pigment will generally comprise less than 5% by weight of said composition.

It maybe preferred to include one or more antioxidants in the composition of the capsule of the present invention. The nature of the antioxidant is not narrowly critical and suitable antioxidants may generally be chosen by those skilled in the art without undue experimentation. Preferred antioxidants include butylated hydroxy anisole and butylated hydroxy toluene.

The capsules of our invention may be used to administer a wide variety of therapeutic agents. Therapeutic agents which are suitable for use in the capsules may include for example, trace elements; bloat prevention agents; antibacterials which may include 5- oxytetracycline, and chlorotetracycline. Penicillins such as ampicillin and penicillin G, aminoglycosides such as neomycin, streptomycin, apramycin, and macrolides such as erythromycin; antibacterial growth promotants such as polymycin and lincomycin; hormonal growth promotants; antiparasitic agents such as amprolium; nutritional agents including vitamins; sulpha drugs; and the endoparasiticides and ectoparasitices described hereinafter. These therapeutic agents may be used alone or in combination.

In a further particular embodiment of our invention we provide capsules prepared from polyethylene glycol compositions as hereinbefore described, wherein said composition in addition comprise one or more therapeutic agents. Suitable therapeutic agents include, for example, trace elements, anti-bloat agents, endoparasiticides such as anthelmintics and flukicides, and systemic parasiticides.

In the embodiment, the therapeutic agent may be present in the capsule composition as a simple solution or as a dispersed phase, such that the therapeutic agent is rapidly released in situ when the capsule dissolves in the rumen fluids. Alternatively, where delayed or timed release of a therapeutic agent is desired, the therapeutic agent may be used in a modified form, such as microencapsulated particles, where a therapeutic agent is included in the capsule composition the processing temperature and conditions used to form the capsules from the compositions may need to be modified to prevent chemical decomposition or degradation of the therapeutic agent, as, in the case of microencapsulation, physical damage.

This embodiment of our invention has several advantages. It provides the means whereby two or more therapeutic agents may be administered in a single treatment with consequent saving in labour and handling costs. Since the capsule composition effectively shields the therapeutic agent as agents contained within the composition from the therapeutic agent or agents within the capsule cavity, it is possible to have a combined treatment for therapeutic agents that are normally difficult or impossible to incorporate in a single treatment because of interaction between the therapeutic agents. Even where compatibility of therapeutic agents is not a particular difficulty, the separate incorporation of agents into the capsule walls and capsule cavity can eliminate the need to develop a special formulation.

There is a further advantage of this embodiment in situations where one particular therapeutic agent is regularly administered, for example on a prophylatic basis, and other therapeutic agents are used less frequently or with a few animals with particular infections or ailments. The end-user can then incorporate the less-frequently required agents in the cavity as and when needed. For this application the capsule is not sealed at the stage of initial manufacture, and the capsule design may incorporate interlocking edges to the cap and body parts so that the capsule parts may be readily fitted together by an end user.

One particular application for the capsule of our invention is in the treatment of trace element deficiencies, in particular copper deficiency, in ruminant animals. This application will be described in more detail to illustrate our invention.

The role of trace elements such as copper, iron, molybdenum, cobalt, nickel, zinc and manganese in ruminant nutrition is well known, and in particular the unusually large requirement of copper by sheep and cattle is well recognised. This deficiency is usually met by the use of a dietary supplement in the form of oral drenching with solid or liquid compositions, or by intramuscular injections. These traditional methods of administration have suffered from various disadvantages. Liquid compositions, such as for example solutions of soluble salts of copper in the case of copper deficiency, are readily administered but are not retained in the animal. Intramuscular injections are limited to soluble forms of copper and typically special organic complexes of the trace elements are required. Even with organic complexes repeated injections are usually necessary. In addition tissue reactions frequently occur at the site of the injection and there is a high risk of acute general toxicity. Attempts have been made to prepare solid bullets or boluses which will remain in the alimentary tract and release copper over long periods but particular difficulties have arisen because of the nature of the digestive system of ruminants.

Insoluble forms of copper, such as the metallic and oxide forms can undergo slow dissolution in the rumen or abomasum but unfortunately the conditions in the rumen are such that the copper rapidly becomes coated with a phosphate or sulphide layer which prevents further dissolution of the copper. Ideally the copper material would not remain in the rumen but pass rapidly to the abomasum where the acid conditions are better suited for the dissociation of metals and metal oxides.

This selective deposition in the abomasum is difficult to achieve since heavy particles will remain in the bottom of the rumen and not reach the abomasum, whereas lighter particles which can transfer readily from the rumen to the abomasum are also readily lost from the abomasum. One approach that has been tried is to use a relatively large solid pellet or plug of a trace element material in combination with a "grinder", typically a grub screw, so that although the solid pellet is retained in the rumen, the action of the grinder is to constantly remove the phosphate or sulphide coatings on the plug thus exposing fresh surface of the plug for dissolution and absorption. This approach ha been used to some extent for treating cobalt deficiency but has not been particularly successful with copper because of the greater susceptibility of that element to coating in the rumen. A further disadvantage of this method is that both the pellets and grinders are hard and can seriously cut and damage the mouth and soft tissue parts of the animal. Various devices have been used to try to place the pellets as near the rumen as possible. Thus there has been an urgent need for better method of treatment of copper deficiency in ruminant animals.

Australian Patent No. 520489 discloses the use of a particular copper-releasing substance, hereinafter referred to a copper oxide needles, for the treatment of copper deficiency in ruminant animals. In this disclosure the particles containing the trace element have a high specific gravity and low mass such that the particles are readily transferred from the rumen but a high proportion are retained in the abomasum to enable partial dissolution and absorption to take place over an extended period of time.

While this method has the potential to overcome some of the difficulties of earlier methods of treatment of trace element deficiencies, it has particular difficulties of its own related to the method of administration to the animals per os. In particular, the elongate particles of trace element material, adapted to move readily from the rumen while remaining in the abomasum, are very fragile. This is particularly so in the case of the copper oxide needles referred to above. It has proved very difficult if not impossible to dose ruminant animals without damage to the elongate particles or needles occurring either by initial chewing by the ruminant animals, or by chewing following regurgitation of the particles or needles and the fragmented particles or needles do not have the ability to be retained in the abomasum and are therefore wastefully excreted. Various forms of pastes or gelatin capsules have been tried without success.

In contrast with the above prior art methods of treating copper deficiency, the capsules of our invention provide a convenient and effective method of administering copper oxide needles. Thus in an embodiment of the present invention there is provided a capsule as hereinbefore described wherein the cavity defined by said capsule contains a particulate source of copper.

There is also provided a method of treating copper deficiency in animals which comprises the administration of a capsule as hereinbefore defined, and having within the capsule cavity a therapeutically effective amount of particulate copper. The preferred form of particulate copper is that of the copper needles disclosed in Australian Patent No 520489. Preferably the copper oxide needles have a size or maximum dimension in the range of from 0.5 to 5.0 millimeters, and a relatively high specific gravity, for example, greater than 2.0 and most preferably greater than 5.0.

It is surprising that the herein described capsules of copper oxide needles are effective since it has long been regarded in the art that boluses or pellets of material administered for treatment of trace element deficiency in ruminants must have a specific greater than 2.0 to avoid regurgitation and expectoration before dissolution of the trace element material can occur. Capsules containing copper oxide needles prepared according to our invention may have specific gravities lower than 2.0 but are nevertheless retained in the rumen for a sufficient length of time for the capsule to first form a gel, and then to dissolve releasing the more dense copper oxide needles.

Without wishing to be bound by theory we believe that the rapid dissolution of the present capsule composition may aid retention of the capsule. In particular the present capsules rapidly form a sticky hydrogel which may cause the composition to adhere to the rumen wall while dissolving and hence not be regurgitated. Capsules of higher polyethylene glycol generally dissolve more rapidly in the animal digestive tract.

The aspect ratio and shape of the capsule for this application is as described hereinbefore and preferably the internal cavity has no dimension which is smaller than the length of the copper oxide needles used.

Typical capsules of our invention used for administration to sheep are short cylinders of outside diameter of ca 11-14 mm and 15-20 mm length.

Typical capsules of the of our invention used for administration cattle are cylinders of outer diameter ca 17-21 mm.

The dose rate is proportional to the body weight of the animal but copper deficiency in sheep can be effectively treated with capsules containing 1.25 g of copper oxide needles for a body weight of for example up to 30 kg, and 2.5 g of needles for animals in excess of 30 kg. It is convenient to use capsules containing 1.25 g of copper oxide needles so that the dosing regime is reduced to a choice of one or two pellets, which could be delivered from an appropriate gun. Alternatively, it is possible to have two pellets containing 1.25 and 2.5 g respectively but if these are of similar external dimensions they may be colour coded or otherwise marked to identify the dose content.

Capsules containing 10 g of copper oxide needles may be particularly suitable for administration to cattle. In general cattle of up to 150 kg may be effectively dosed with 10 g of copper oxide needles. Cattle over this weight may generally be dosed with 20 g of copper oxide needles.

In a yet further preferred embodiment of our invention we provide capsules as hereinbefore described containing copper oxide needles wherein the said capsule composition additionally comprises one or more therapeutic agents for the control of endoparisitic infections.

By endoparasitic infections we mean gastrointestinal and pulmonary nematodes such as, for example, Haemonchus spp, Ostergagia spp, *Trinchos tronglus* spp, Nematodirus spp, Oesophagostomum spp, Chabertia spp, and Dictyocaulus spp and liver fluke such as, for example Fasciola spp.

Suitable therapeutic agents for the control of gastrointestinal and pulmonary nematodes include, for example, thiabendazole, banminth trade name, parbendazole, cambendazole, mebendazole, oxbendazole, fenbendazole, albendazole, oxfendazole, morantel, oxyclozanide niclosamide, rafoxanide, nitroxynil, febantel and tetramisole.

A particular preferred therapeutic agent for inclusion in the compositions of our invention is the active isomer of tetramisole, namely levamisole. Tetramisole is the common name for the hydrochloride salt of the anthelmintic d1-2,3,5,6-tetrahydro-imidazo [2,3-b] thiazole, and levamisole is the common name for the laevorotatory isomer of tetramisole.

We have found that the capsules of the present composition are particularly resilient and resist breakage and cracking. When filled with a heavy material such as copper oxide needles the capsules show high resistance to breakage and bursting even during multiple dosing by means of dispensing guns as hereinbefore described.

Even though they generally show a greater resilience than capsules heretofore used in the art the present capsules readily dissolve in the digestive tract of animals to release the therapeutic agent or agents.

This invention is now illustrated by but not limited to the following examples in which all parts and percentages are on a weight basis unless otherwise specified.

EXAMPLE 1

Figure 5:
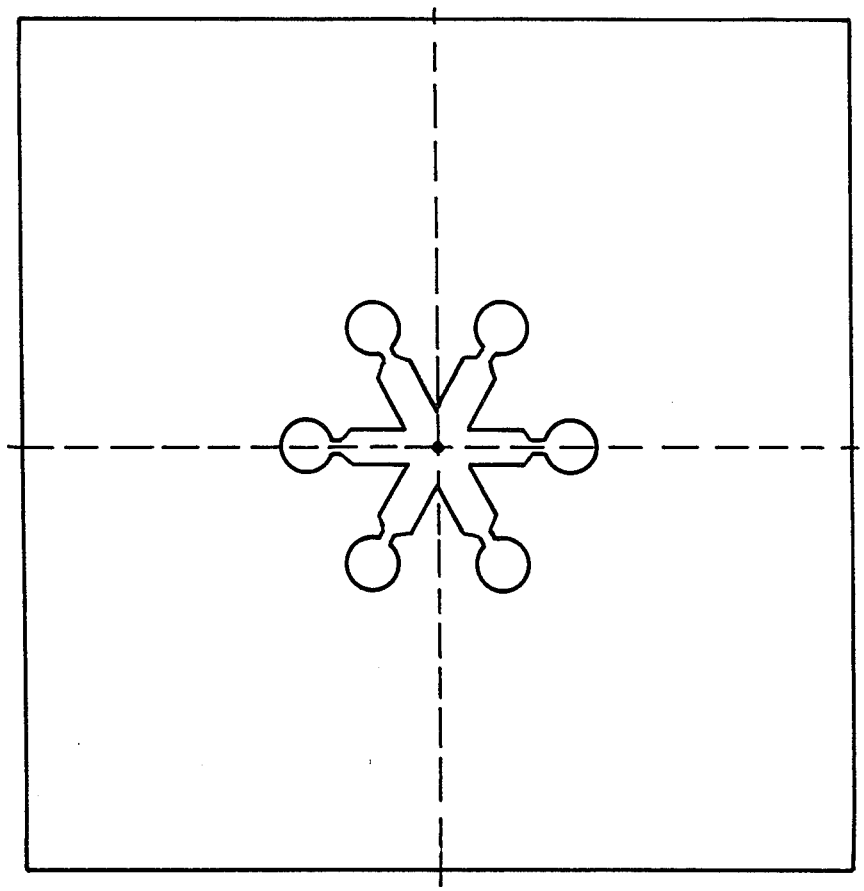

Capsules which may be used in the delivery of therapeutic agents to sheep or cattle were prepared as follows. A mixture of 350 grams of "Polyox" WSR 205 (a poly (ethylene oxide) of approximate molecular weight 600,000), 600 grams of PEG 4000 (a polyethylene glycol of approximate molecular weight 4000), 50 grams of calcium carbonate, 2 grams of butylated hydroxy toluene and 2 grams of butylated hydroxy anisole were thoroughly mixed in a powder blender. This mixture was injection moulded using a 3 oz Johns 75-IXT-¾ injection moulder operating under the following conditions:

Temperatures—100° C. in Zone 1, 130° C. in Zone 2, 140° C. in Zone 3, 140° C. in the nozzle; injection pressure 8100 psi (569.5 kg/cm$^2$); mould temperature 10° C.; cycle time 20 seconds. The die was designed to produce capsules with the dimensions shown in FIG. 3 such that each moulded unit contained 3 body and 3 head capsule halves. The design of the moulding plate of the die for the production of these capsules is shown in FIG. 5. The die was designed so that the cooled unit was pushed off the moulding plate of the die by six pins of diameter 8 mm which remained stationary as the remainder of the die recoiled at the completion of each cycle. With a cycle time of 20 seconds, approximately 540 capsules were produced hourly. The capsule head and body parts were readily detached from the internal portion of the moulded unit by the action of a sharp blade.

Head and body sections could be fitted together providing a smooth exterior join.

EXAMPLE 2

Capsule head and body parts were prepared according to Example 1. Into the body parts of each capsule were placed 1.25 g of copper oxide needles of the form disclosed in Australian Patent No. 520 489. The sleeve of each body part was wetted with approximately 1 µL of water and the head parts were then pushed onto the body parts to give a smooth join.

Alternatively the capsule parts were first pushed together to give a smooth join and bonded.

EXAMPLE 3

Capsules which may be of particular use in the delivery of copper oxide needles to cattle were prepared as follows. A mixture of 350 grams of "Polyox" WSR 205; 600 grams of PEG 4000, 50 grams of calcium carbonate, 2 grams of butylated hydroxy toluene and 2 grams of butylated hydroxy anisole was prepared in a powder blender. This mixture was injection moulded using a 30 oz Johns 75-IXT-¾ injection molder operating under the following conditions:

temperatures—70° C. in Zone 1, 100° C. in Zone 2, 130° C. in Zone 3 and 150° C. in the nozzle; injection pressure 9000 psi (633 kg/cm$^2$); mold temperature 8° C.; cycle time 20 seconds.

Figure 4:
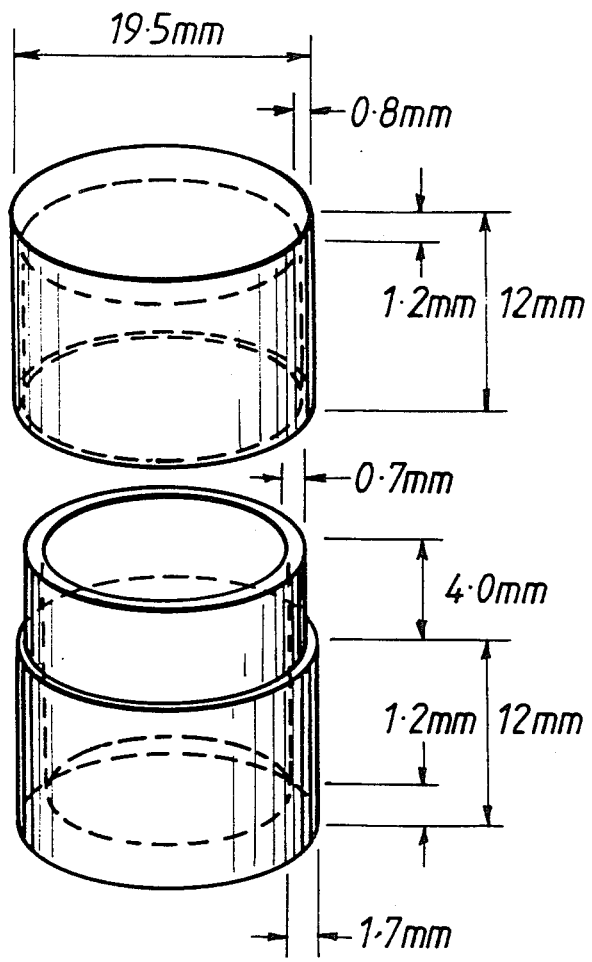
FIG. 4 shows head and body portions of a capsule which may be convenient size for administration to cattle. The capsule may be suitable for administration by means of a dispensing gun suitable for the purpose.

The die was designed to produce capsules with the dimensions shown in FIG. 4, and was of the same basic design as the die for the production of capsules for the delivery of copper oxide needles to sheep shown in FIG. 5 with the appropriate modifications to produce the larger capsules. The molded unit was similarly ejected from the die and converted to the filled capsule as described in Example 1 and Example 2.

Examples 4–16

Capsules of the dimensions shown in FIG. 3 were prepared by the procedure of Example 1 using different compositions.

The composition used in each example is listed in the following table. (Table No 1).

TABLE NO 1

| Example No | COMPOSITION PARTS BY WEIGHT | | | | | | | | | |
|---|---|---|---|---|---|---|---|---|---|---|
| | PEG | PO | TALC | CaCO₃ | BHA | BHT | TiO₂ | YO | RO | UB |
| 4 | 20 | 80 | — | — | — | — | — | — | — | — |
| 5 | 40 | 60 | — | — | 0.2 | 0.2 | — | — | — | — |
| 6 | 60 | 40 | — | — | 0.2 | 0.2 | — | — | — | — |
| 7 | 20 | 50 | 30 | — | 0.2 | 0.2 | — | — | — | — |
| 8 | 20 | 50 | — | 30 | 0.2 | 0.2 | — | — | — | — |
| 9 | 40 | 40 | — | 20 | 0.2 | 0.2 | — | — | — | — |
| 10 | 50 | 40 | — | 10 | 0.2 | 0.2 | — | — | — | — |
| 11 | 55 | 40 | — | 5 | 0.2 | 0.2 | — | — | — | — |
| 12 | 55 | 40 | — | 5 | 0.2 | 0.2 | — | 0.1 | — | — |
| 13 | 60 | 35 | — | 5 | 0.2 | 0.2 | 1 | — | — | — |
| 14 | 60 | 35 | — | 5 | 0.2 | 0.2 | — | 1 | — | — |
| 15 | 60 | 35 | — | 5 | 0.2 | 0.2 | — | — | 1 | — |
| 16 | 60 | 35 | — | 5 | 0.2 | 0.2 | 0.5 | — | — | 0.5 |

PEG — PEG 4000 (a polyethylene glycol of approximate molecular weight 4000
PO — "Polyox" WSR 205 a poly (ethylene oxide) of approximate molecular weight 600,000 ("Polyox" is a trade mark).
Talc — Food grade talc
CaCO₃ — Food grade calcium carbonate
BHA — Butylated Hydroxy Anisole
BHT — Butylated Hydroxy Toluene
TiO₂ — Powdered Titanium Oxide
YO — Yellow Ochre
RO — Red Ochre
UB — Ultramarine Blue

EXAMPLE 17

Capsules prepared according to Example 1 were each filled with 1.25 g of copper oxide needles according to Example 3.

Administration of these capsules was examined for one hundred and sixty-two Merino and crossbred wethers (each of approximate weight 24 kg) which had been grazing in ryegrass/subclover. Administration was by means of a commercially available pellet gun.

Procedure and results of the administration test were as follows:
(a) Sixty-two sheep were each dosed with a single capsule immediately after being removed from pasture. The animals were held on concrete for 3 hours post-dosing. No capsules were regurgitated during this time.
(b) A further 50 sheep were held off pasture for 4 hours then each dosed with a single capsule. The animals were held on concrete for 3 hours post-dosing and no capsules were regurgitated during this time.
(c) 50 Sheep were withheld from feed for 24 hours and then each dosed with one capsule. The animals were held on concrete for 3 hours post-dosing and no capsules were regurgitated during this time.

EXAMPLE 18

283 Merino cross breed ewes, wethers and lambs taken directly off pasture were dosed using commercially available pellet gun with capsules, prepared according to Example 1, filled with either 1.25 gram of copper oxide needles (for animals less than 30 kg) or 2.5 gram (for animals greater than 30 kg). The sheep were held on a concrete floor for three hours and monitored for regurgitation. No capsules or needles were regurgitated during this time.

EXAMPLE 19

299 Morino cross ewes and lambs held off pastures for 4 hours were dosed using a commercially available pellet gun with capsules, prepared according to Example 1, filled with the appropriate dose of copper oxide needles according to body weight as described in Example 19. The sheep were held on a concrete floor for three hours and monitored for regurgitation. No capsules or needles were regurgitated during this time.

EXAMPLE 20

328 Morino cross ewes, wethers and lambs held off pasture for 24 hours were dosed using a commercially available pellet gun with capsules, prepared according to Example 1, filled with the appropriate dose of copper oxide needles according to body weight as described in Example 19. The sheep were held on a concrete floor for three hours and monitored for regurgitation. No capsules or needles were regurgitated during this time.

EXAMPLE 21

98 Simmental cows and heifers, held 18 hours off pasture were each dosed with 2 cpasules, prepared according to Example 3, filled with 10 grams of copper oxide needles. The cattle were held on a concrete floor for 3 hours and monitored for regurgitation. One capsule was regurgitated during this time.

EXAMPLE 22

50 Cross bred Hereford cows, taken directly off pasture, were each dosed using a commercially available pellet gun with two capsules, prepared according to Example 3, filled with 10 grams of copper oxide needles. The cows were held on a concrete floor for three hours and monitored for regurgitation. No capsules were regurgitated during this time.

EXAMPLE 23

242 Simmental cows and calves taken directly off pasture were each dosed using a commercially available pellet gun, with 2 capsules, prepared according to Example 3, filled with 10 grams of copper oxide needles. The cattle were held on a concrete floor for three hours and monitored for regurgitation. 4 Capsules were regurgitated during this time.

EXAMPLE 24

Eleven first-cross merino sheep were dosed using a commercially available pellet gun with capsules prepared according to Example 1 filled with either 1.25 g copper oxide needles (animals with body weight less than 25 kg) or 2.5 gm copper oxide needles (animals with body weight greater than 25 kg). A further 12 sheep were not treated. Hepatic copper levels for all animals were determined after zero, four and eight and thirteen weeks and are shown below.

|  | No of sheep | Average liver copper levels (mmol/kg dry matter) | | | |
| --- | --- | --- | --- | --- | --- |
|  |  | 0 weeks | 4 weeks | 8 weeks | 13 weeks |
| Treated with copper oxide needles | 11 | 1.00 | 4.90 | 7.35 | 6.89 |
| Untreated | 12 | 1.18 | 1.39 | 1.97 | 2.48 |

No aminals in the treated group exceeded the World Health Organization maximum liver copper level of 11.4 mmol/kg DM. The incease in liver copper levels for the untreated group were due to seasonal increase in pasture copper levels.

COMPARATIVE EXAMPLE 1

A mixture of 1000 grams of "Polyox" WSR 205, 2 grams of butylated hydroxy toluene and 2 grams of butylated hydroxy anisole was prepared in a powder blender. This mixture could not be successfully injection moulded using a 30 oz Johns 75-IXT-¾ injection molder since unacceptably high back pressures (at least 18,000 psi (1266 kg/cm$^2$) which is the upper pressure limit of the 3 oz Johns injection molder) and high temperatures (~200° C.) were required. When 10% PEG 4000 was incorporated into the mixture, injection molding became possible, with injection pressure at 17,000 psi and nozzle temperature at 200° C.

COMPARATIVE EXAMPLE 2

A mixture of 200 grams of "Polyox" WSR 205, 800 grams of PEG 4000, 2 grams of butylated hydroxy toluene and 2 grams of butylated hydroxy anisole was prepared in a powder blender. When attempts were made to injection mold this mixture, it was found that it was not thermoplastic.

COMPARATIVE EXAMPLE 3

This is a comparative example of a paste formulation of copper oxide needles (CON) used to treat copper-deficient ruminants.

First-cross merinos (ca 30 kg) each received 3 ml (equivalent to 2.5 g CON) of the following paste formulations from a commercial veterinary paste gun.

Formulation No 1

CON (30 g) in 19 ml of a paste prepared from Attagel 40 (50 g) and distilled water.

Formulation No 2

CON (30 g) in 19 ml of a paste prepared from Volclay 325 (500 g) and distilled water (200 ml).

Formulation No 3

CON (30 g) in 19 ml of a paste prepared from PEG 300 (50 g) and PEG 1500 (50 g).

In all these cases, although the paste was swallowed readily, the copper oxide needles were chewed and seriously fragmented.

I claim:

1. A capsule for administration to an animal of at least one therapeutic agent, the composition of the capsule comprising
   (i) from 10–75% by weight of at least one polyalkylene glycol of average molecular weight 2,000–20,000; and
   (ii) from 20–80% by weight of poly(ethylene, oxide) of average molecular weight 80,000–1×10$^7$.

2. A capsule according to claim 1, wherein the polyalkylene glycol is selected from at least one of the group consisting of polyethylene glycol, polypropylene glycol, the condensation product of one mole of nonylphenol with 100 moles of ethylene oxide, the condensation product of one mole of octylphenol with 100 moles of ethylene oxide and the condensation product of a C$_{16}$ fatty acid alcohol and 50 moles of ethylene oxide.

3. A capsule according to claim 1, wherein the polyalkylene glycol is a polyethylene glycol of average molecular weight from 2,500–6,000.

4. A capsule according to claim 1, wherein the polyethylene glycol has a molecular weight of from 3,000–5,000.

5. A capsule according to claim 1, wherein the poly(ethylene oxide) has an average molecular weight of from 1×10$^5$–1×10$^6$.

6. A capsule according to claim 1, wherein the poly(ethylene oxide) has an average molecular weight of from 300,000–800,000.

7. A capsule according to claim 1, wherein the ratio of polyethylene glycol to poly(ethylene oxide) is from 0.15–2.5.

8. A capsule according to claim 1, wherein the ratio of polyethylene glycol to poly(ethylene oxide) is from 0.5–2.5.

9. A capsule according to any one of claims 1, wherein the ratio of polyethylene glycol to poly(ethylene oxide) is from 1–2.5.

10. A capsule according to claim 1, wherein the composition of the capsule comprises
    (i) 35–75% by weight of polyethylene glycol of average molecular weight of from 2,000–12,000; and
    (ii) 25–65% by weight of poly(ethylene oxide) of average molecular weight of from 1×10$^5$–1×10$^7$.

11. A capsule according to claim 10, wherein the composition of the capsule comprises from 50–70% by weight of the polyethylene glycol and from 35–50% by weight of the poly(ethylene oxide).

12. A capsule according to claim 1, wherein the composition of the capsule comprises therapeutic agents.

13. A capsule according to claim 1, wherein the therapeutic agent comprised in the composition of the capsule and a therapeutic material contained in the cavity defined by the capsule are different.

14. A capsule according to claim 1, wherein the cavity defined by the capsule contains at least one trace element.

15. A capsule according to claim 14, wherein the trace element is a particulate source of copper.

16. A capsule according to claim 15, wherein the trace element is copper oxide needles.

17. A capsule according to claim 16, wherein the copper oxide needles have a maximum dimension of from 0.5 to 5.0 mm.

18. A capsule according to claim 16, wherein the copper oxide needles have a specific gravity of greater than 2.

19. A capsule according to claim 18, wherein the specific gravity is greater than 5.

20. A capsule according to claim 16, wherein the composition of the capsule comprises at least one therapeutic agent for the control of endoparasitic infections.

21. A capsule according to claim 20, wherein the therapeutic agent for the control of endo-parasitic infections is levamisole.

22. A capsule according to claim 1, wherein the capsule comprises a head part and a body part which fit together such that the diameters of both head and body part at the point of their exterior junction are identical.

23. A capsule according to claim 1, wherein the capsule is approximately cylindrical in shape.

24. A method of administering to an animal at least one therapeutic agent which comprises administering to the animal at least one capsule according to claim 1.

25. A method of treating copper deficiency in an animal which comprises administering to the animal at least one capsule according to claim 15.

* * * * *